United States Patent [19]

Brizgis et al.

[11] Patent Number: 4,713,781
[45] Date of Patent: Dec. 15, 1987

[54] GRAIN DAMAGE ANALYZER

[75] Inventors: Lawrence J. Brizgis, Moline, Ill.; Daniel B. Keleher, Bettendorf, Iowa; Vernon D. Bandelow, Cambridge, Ill.

[73] Assignee: Deere & Company, Moline, Ill.

[21] Appl. No.: 777,886

[22] Filed: Sep. 19, 1985

[51] Int. Cl.$^4$ .................... G06F 15/20; G06G 7/48; H01J 40/14
[52] U.S. Cl. ............................ 364/552; 382/51; 358/107; 358/169; 250/222.2; 250/223 R
[58] Field of Search .............. 364/552; 250/222.2, 250/223 R; 382/7, 51; 358/93, 107, 166, 167, 169

[56] References Cited

U.S. PATENT DOCUMENTS

| | | | |
|---|---|---|---|
| 3,776,642 | 12/1973 | Anson et al. | 356/418 |
| 3,828,173 | 8/1974 | Knepler | 364/498 |
| 3,861,788 | 1/1975 | Webster | 356/418 |
| 4,037,970 | 7/1977 | Webster et al. | 356/418 |
| 4,246,098 | 1/1981 | Conway et al. | 250/223 R |
| 4,260,262 | 4/1981 | Webster | 364/526 |
| 4,344,146 | 8/1982 | Davis, Jr. et al. | 364/552 |
| 4,493,106 | 1/1985 | Farhangi et al. | 382/51 |
| 4,509,195 | 4/1985 | Nadler | 382/51 |
| 4,519,041 | 5/1985 | Fant et al. | 364/552 |
| 4,561,018 | 12/1985 | Berthel et al. | 250/223 R |
| 4,572,666 | 2/1986 | Satake | 250/223 R |
| 4,587,617 | 5/1986 | Barker et al. | 358/107 |

OTHER PUBLICATIONS

Berlage et al., "Seed Sorting by Machine Vision", Agricultural Engineering, Oct. 1984, pp. 14–17.
Kranzler, "Applying Digital Image Processing in Agricultural Engineering, Mar. 1985, pp. 11–13.

Primary Examiner—Errol A. Krass
Assistant Examiner—Danielle Laibowitz

[57] ABSTRACT

A grain damage analyzer illuminates a grain sample with longwave, ultraviolet radiation, causing the exposed starch of the damaged portions to fluoresce and a video camera views the illuminated grain. The video signal from the camera is digitized into an array of pixels. The number of percentage of pixels which have an intensity exceeding a predetermined threshold represents the extent of damage to the sample.

10 Claims, 6 Drawing Figures

Microfiche Appendix Included
(1 Microfiche, 26 Pages)

GRAIN DAMAGE ANALYZER

BACKGROUND OF THE INVENTION

This application includes a microfiche appendix including one microfiche and 26 frames.

This invention relates to a system for automatically measuring the damage status of seeds or grain.

For various reasons, it is desirable to have a reliable system for measuring the amount of mechanical damage done to samples of grain, such as corn. One reason would be to aid in the evaluation of different grain harvesting or handling mechanisms. Another reason would be to evaluate the grain itself. Currently, the USDA endorses a sizing technique to determine grain damage. This technique does not detect kernels which are slightly chipped or cracked. Another technique uses a dye which visually enhances any damage done to kernels. This technique requires significant sample preparation and then manual sorting and analysis of the sample, and is subjective and time consuming.

Known grain analysis systems are described in U.S. Pat. No. 3,776,642, issued Dec. 4, 1973 to Anson et al and in U.S. Pat. No. 3,828,173, issued Aug. 6, 1974 to Knepler. These systems are designed to determine the constituents of a grain sample, such as the amount of oil, protein and moisture therein. Both systems function by analyzing infrared radiation reflected from the sample. In neither system is an image of the grain sample formed or analyzed, nor is damage determined.

It has been suggested by Berlage et al that machine vision and digital image analysis techniques could be used to sort and separate seeds from contaminants such as unwanted crop seeds, weed seeds, and inert matter such as plant parts, fungal bodies and soil particles, (see "Seed Sorting by Machine Vision" by Berlage et al, *Agricultural Engineering*, October 1984. However, the Berlage et al article does not include the information required to measure grain damage utilizing machine vision.

SUMMARY OF THE INVENTION

An object of the present invention is to provide a grain damage analysis system which is fast, accurate and objective and which yields consistent results.

Another object of the present invention is to provide a grain damage analysis system utilizing machine vision.

Another object of the present invention is to provide a grain damage analysis system utilizing digital image processing techniques.

These and other objects are achieved by the present invention which includes a mixer which holds and mixes a sample of grain to be analyzed. A lamp illuminates the grain sample with ultraviolet radiation, causing the exposed starch portions of the grain to flouresce to thereby produce a visual contrast between the damaged and undamaged portions of the grain sample. A video camera produces an image of the illuminated sample and sends a video signal to a computer. The computer digitizes the video signal into an array of pixels, each with a value representing the intensity of a corresponding part of the image. The computer determines the percentage of pixels which have values which exceed a predetermined threshold. This percentage is related to the amount of exposed starch, and thus, the extent of the grain damage. The computer automatically analyzes a plurality of images of each sample and automatically controls the mixer so that each sample is mixed before an image is analyzed.

DETAILED DESCRIPTION

Figure 1:
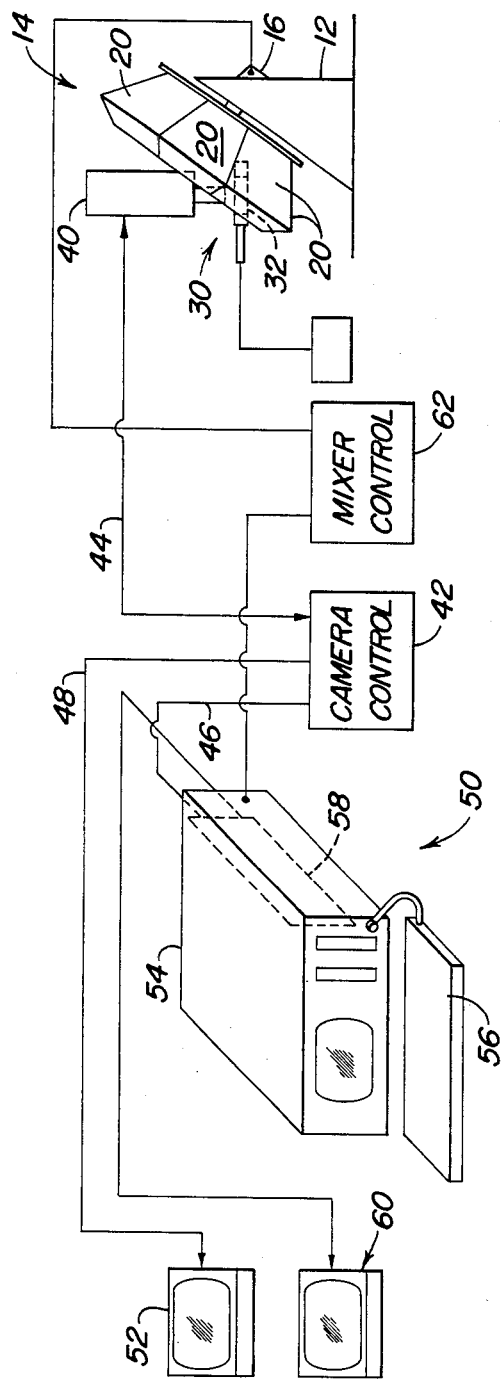
FIG. 1 is a schematic diagram of a grain damage analyzer constructed according to the present invention.
Figure 2:
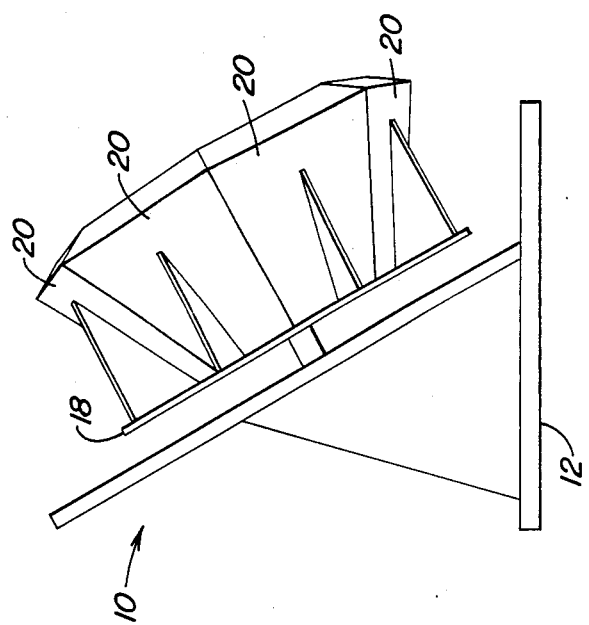
FIG. 2 is a view of a mixer apparatus of the present invention, viewing along its axis of rotation.
Figure 3:
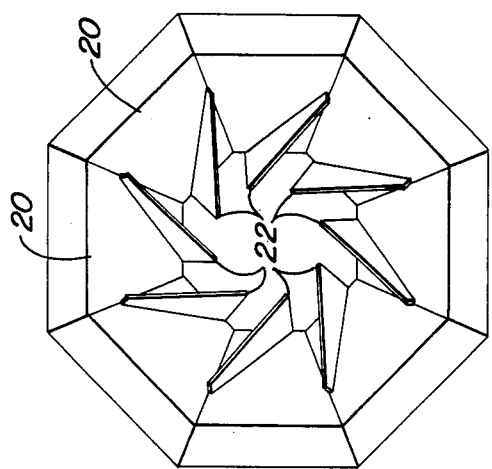
FIG. 3 is a side view of the mixer of FIG. 2.

The grain damage analyzer includes a rotary mixer 10 into which is placed the grain sample to be analyzed. The mixer 10 includes a base 12 which supports a mixer bowl 14 for rotation about an axis which is at a desired angle with respect to horizontal, such as 30 degrees. The bowl 14 is mounted on the shaft of a conventional 12-volt DC gear motor 16 (or the equivalent). The bowl 14 includes a flat disc 18 from which extends a plurality (8, for example) of trapezoidal-shaped panels 20. The bowl 14 is constructed so that whichever panel is rotated into the lowermost position, the surface of that lowermost panel will be nearly horizontal. The bowl 14 also includes a plurality of triangular mixing paddles 22, each extending between the disc 18 and the joint between each adjacent pair of panels 20. When a grain sample is placed in the bowl 14, the paddles stir the sample as the bowl rotates to move a different panel 20 into the lowermost position. For reasons which will become apparent later, the interior of bowl 14 preferably has a coating which is nonflourescing and nonreflective of visible and ultraviolet light.

A radiation source or lamp 30 is positioned, as shown in FIG. 1, so as to illuminate the grain sample which rests on the lower panel of the bowl 14. The lamp 30 is in the form of a ring surrounding a central viewing opening 32. The lamp 30 is preferably an ultraviolet lamp, such as a Mic-O-Lite I, FUV-36 lamp, available from Astro Grid Lamp Products, Inc. (or the equivalent). This lamp is provided with its own power supply 31. This lamp transmits longwave ultraviolet radiation at about 3650 angstroms wavelength. It is believed that this radiation causes only the exposed starch portions of broken or cracked grain in the sample to flouresce or luminesce. In otherwords, the exposed starch portions will absorb the ultraviolet radiation and then emit visible light. It is believed that this fluorescense increases the contrast between the damaged and undamaged portions of the grain.

The light emitted by the grain sample in mixer 10 is received by a video camera 40 which is positioned so that its field of view extends through the lamp opening 32 and includes the grain sample on the lowest panel 20 of the mixer bowl 14. The camera 40 is connected to an associated camera control unit 42. The camera control unit 42 includes controls for the remote camera 40, it receives a video signal from camera 40 over a cable 44 and it provides video signals over standard coaxial, shielded cables 46 and 48 to a computer 50 and to a video monitor 52, respectively. A suitable camera and control unit would be the 67M Series TV camera system available from DAGE-MTI, Inc. with a Super Chalnicon R tube and an F1.4 25 mm lens, although other similar camera systems could be utilized as well. In operation, the camera 40 and mixer 10 are preferably surrounded by an opaque shroud (not shown) so that the grain sample and camera are not exposed to ambient light.

The computer 50 may be a Sanyo MBC 775 Portable 256 k with a disc drive and color monitor unit 54 and keyboard 56. A video digitizing system 58 is installed in computer 50.

A suitable digitizing system is the commercially available PC-EYE (TM) Series 1000 Video Capture System. This system includes an interface card 58 and utility software on a floppy diskette (not shown). The interface card receives the analog video signal from cable 46 and provides a digitized 640 by 200 array of 6-bit pixels (allowing 64 grey levels). Signals representing this pixel array are communicated to the computer 50 and to another video monitor 60. Both video monitors 52 and 60 may be Hitachi VM-910A, nine-inch black and white monitors, or any such similar video monitor.

Figure 4:
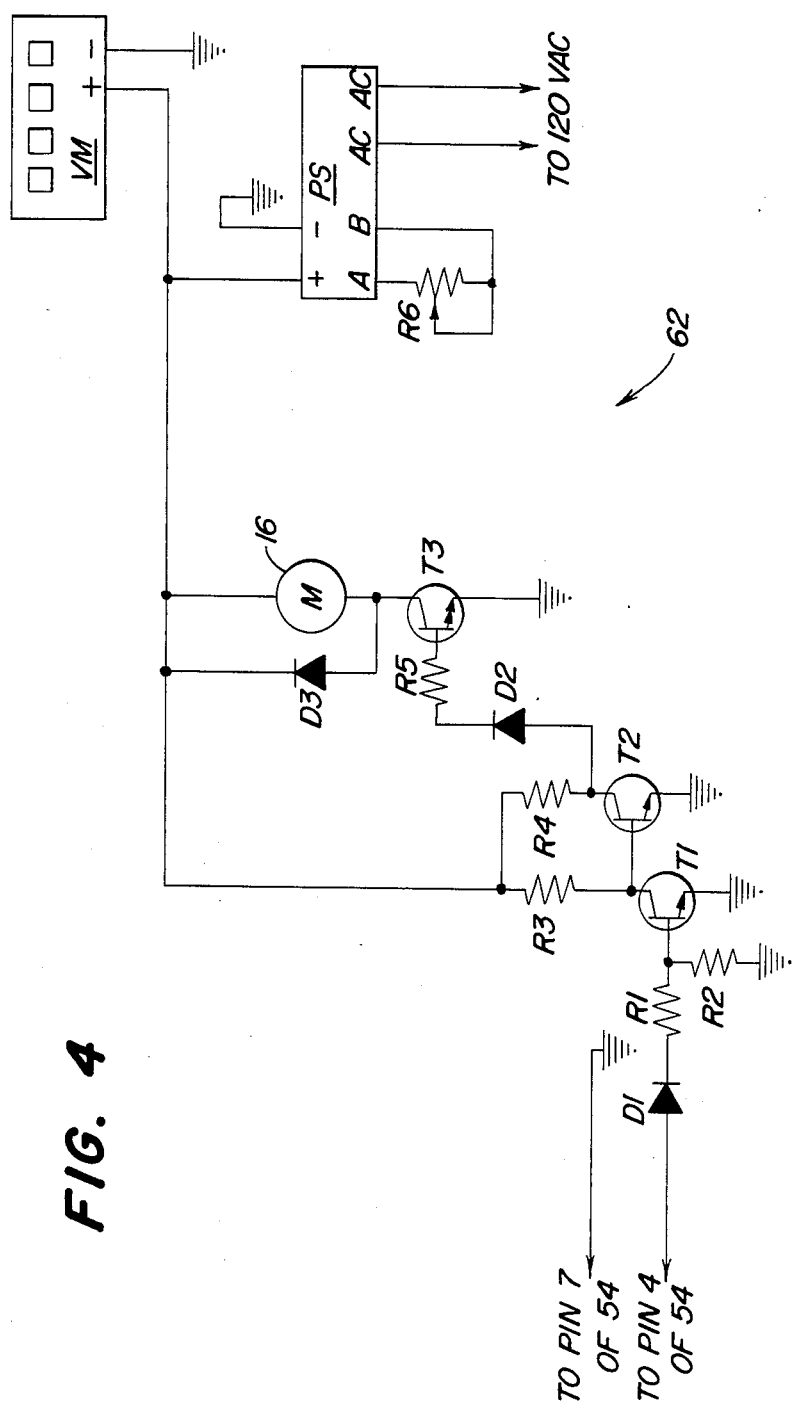
FIG. 4 is a circuit diagram of the mixer control unit of the present invention.

A standard RS 232 serial port of computer 54 is connected to a mixer control circuit 62, seen in detail in FIG. 4. The mixer control circuit 62 responds to binary on-off signals generated by the computer 54 by controlling current flow through mixer motor 16. The output of circuit 62 may be adjusted anywhere between 0 and +12 volts, but is preferably set at +9 volts. Thus, when the signal from computer 54 is low, no current flows through motor 16. When the computer output signal is high, transistor T3 conducts and current flows through motor 16.

Circuit 62 preferably includes the following components, although other components and component values would suffice as well:

| | |
|---|---|
| R1 Resistor | 5.11 k Ohms |
| R2 Resistor | 2.0 k Ohms |
| R3 Resistor | 7.5 k Ohms |
| R4 Resistor | 5.11 k Ohms |
| R5 Resistor | 4.75 k Ohms |
| R6 Potentiometer | 0-1000 Ohms |
| D1,D2 Diodes | IN 914 |
| D3 Diode | IN 4004 |
| T1,T2 Transistors | 2N2222A |
| T3 Transistors | TIP122 |
| PS Power Supply | Emerson ECV 12 N 1.7 |
| VM Voltmeter | Martel Model 3554/2 0-20 VDC |

Figure 5:
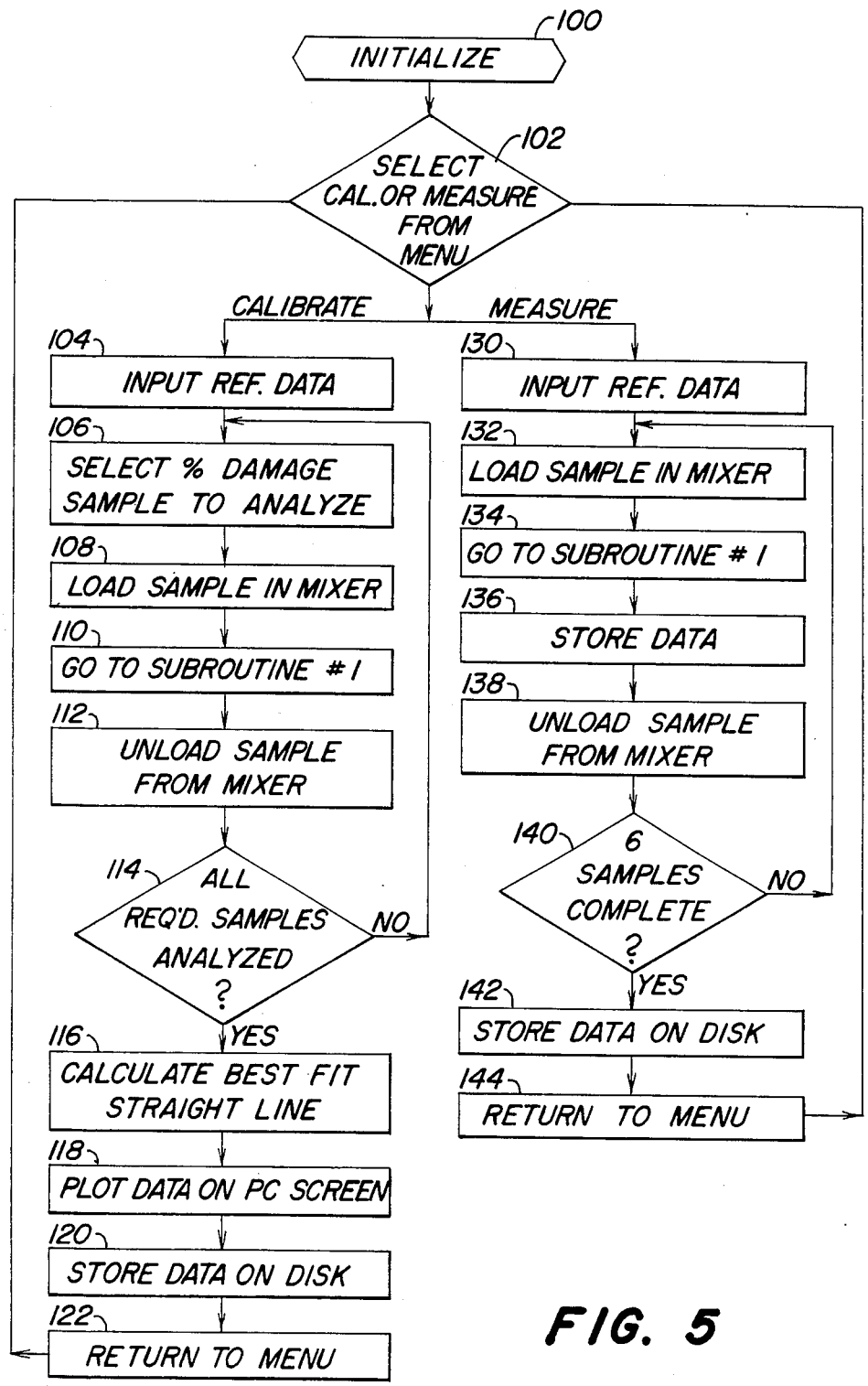
FIG. 5 is a flow chart or a logic flow diagram of the main program or algorithm executed by the present invention.
Figure 6:
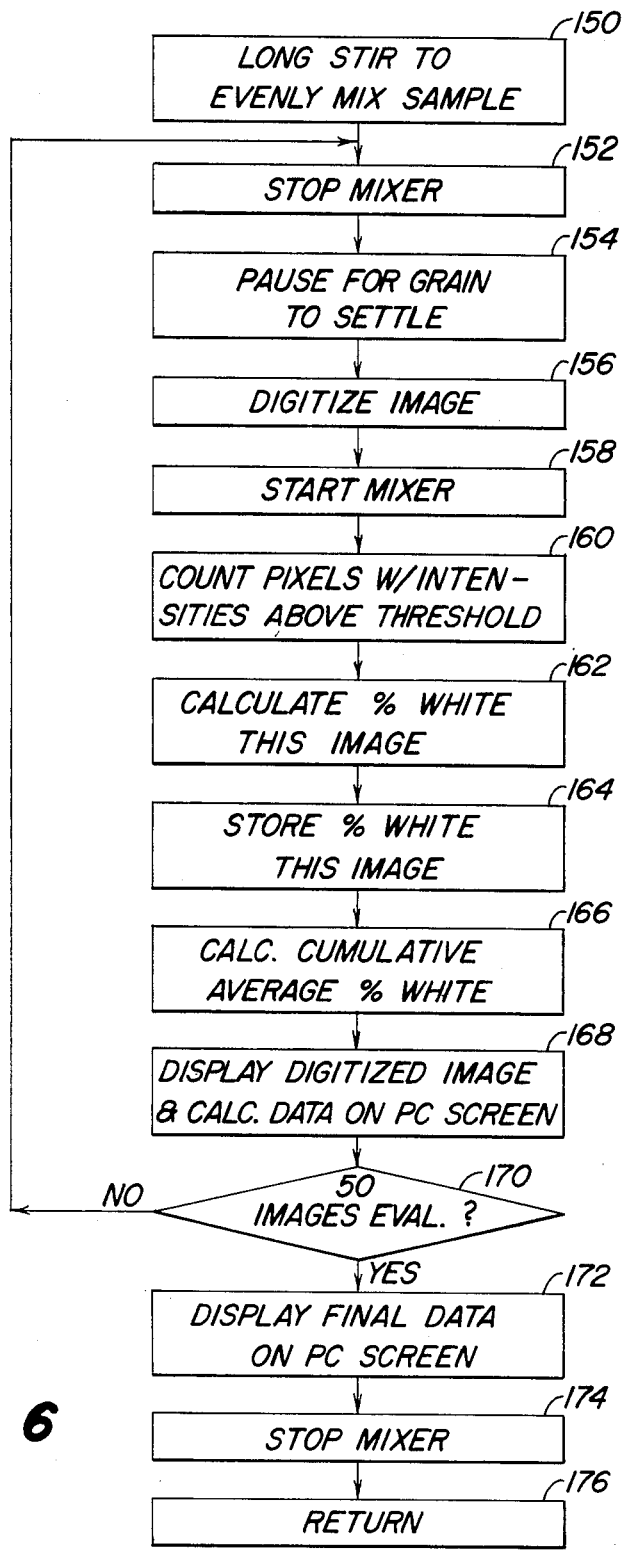
FIG. 6 is a flow chart of a subroutine executed by the present invention.

The computer 54 executes an algorithm which will now be described with reference to FIGS. 5 and 6. For further details concerning the algorithm, the reader is referred to the exemplary computer program listing in the microfilm appendix.

The algorithm begins by initialization in step 100, then either the calibration or measurement branch is chosen in step 102. The calibrate branch begins at step 104 where various user defined, record-keeping information may be entered. At step 106, the percent damage value for a known grain sample is entered. Preferably, the system is calibrated using a number of samples having different, but known, percent damage ratings, such as 0, 10, 20, 30, and 40 percent damage. Then, in step 108, the user is instructed to load the selected sample into the mixer 10. Step 110 then calls up subroutine #1 which will now be described with reference to FIG. 6.

Subroutine #1 begins at step 150 wherein a signal is generated which causes mixer control 62 to energize motor 16 of mixer 10 so that the grain sample is stirred for a relatively long period, such as 5-8 seconds, for example. At the end of this period, the mixer 10 is stopped at step 152. Then, step 154 permits the sample to settle for a certain time period, such as 3 seconds, for example.

Then, at 156, the video signal from camera 40 (which represents an image of the settled grain sample), is digitized according to the software associated with the interface card 58. Thus, the image is represented by a 640 by 200 array of pixels, each having a binary number (0-63) representing the brightness of a corresponding portion of the image.

After the image is digitized, step 158 causes the mixer 10 to start so that the grain sample can be mixed while this digitized image is further analyzed, as follows.

In step 160, a count is obtained of the number of pixels which have brightness levels which exceed a predetermined threshold. This threshold may be established by appropriate adjustment of the "black" and "white" settings (not shown) on the interface card 58. For example, both settings may be adjusted to the same value, such as between 38 and 42, so that for an undamaged corn sample, only 0.2% to 0.4% of the pixels will have values which exceed the threshold.

Then, in step 162, this count is converted into a "percent white" value which is the percentage of pixels which exceed the threshold. This "percent white" value is then stored at step 164. Then, in step 166, a cumulative average percent white value is determined for all the images related to this particular grain sample.

Then, step 168 causes the digitized image to appear on the display of computer 54 along with the data determined in steps 160, 162 and 166. If less than a certain number (50, for example) of images have been processed, then step 170 directs the algorithm back to step 152 to stop mixer 10 and to process another image. Otherwise, the algorithm proceeds to step 172 which causes the final data from steps 160, 162 and 166 to be displayed on the screen of computer 54. Finally, step 172 stops the mixer 10 and step 174 causes a return to the main program.

Referring once again to FIG. 5, the calibrate branch continues at 112 where the operator is directed to unload the known grain sample from mixer 10. Step 114 directs the algorithm back to step 106 for processing of another known grain sample; otherwise, the algorithm proceeds to step 116. Preferably, a series of grain samples having known amounts of damage are processed by the calibration branch. For example, it is preferred to analyze samples with known damage values of 0, 10, 20, 30 and 40%.

Then, step 116 determines a straight-line or other suitable function, best fit relationship between the known damage values and the measured cumulative average percent white values. Then, at step 118, this relationship and the underlying data are displayed on the screen of computer 54. Step 120 causes this data to be stored, such as on disk storage. Step 122 causes the algorithm to return to step 102 so that the operator can again select either the calibrate or measurement branch.

The measurement branch begins at step 130 where various user-defined, record-keeping information may be entered. Then, at step 132, the operator is instructed to load a sample with unknown damage into the mixer 10. Then, step 134 directs the algorithm to the subroutine previously described with reference to FIG. 6 and including steps 150–176.

After the subroutine is executed, the algorithm returns to step 136 which causes the data generated by the subroutine to be stored. Step 138 then instructs the operator to unload the sample from the mixer. If less than six samples have been analyzed, step 140 causes the algorithm to repeat steps 132–138. Preferably, for a quantity of grain of unknown damage rating, a plurality of (such as six) small samples (such as an 8–12 oz. cup) are randomly obtained and then analyzed to obtain a cumulative average percent white value corresponding to the damage rating of this sample. This reduces the chances of error which could occur if only a single, unrepresentative sample is analyzed. After six samples are analyzed, then the analysis data is stored at step 142, after which step 144 causes a return to menu-select step 102.

The cumulative average percent white value obtained from steps 130–144 and the straight line relationship determined in step 116 may then be used to establish the percent damage value for the unknown sample.

While the invention has been described in conjuction with a specific embodiment, it is to be understood that many alternatives, modifications and variations will be apparent to those skilled in the art in light of the aforegoing description. For example, this analysis technique could be used in a grain harvesting mechanism, such as a combine or in other grain handling equipment. Of course, in a combine, there would be no need for the mixing apparatus. Instead, a lamp and camera would be placed in the vicinity of a grain transporting portion of the machine. This could be accomplished with hardware components of reduced size. The resulting damage signal could even be used as an input to a real-time control system, if a sufficiently powerful and fast computer were used. Accordingly, this invention is intended to embrace all such alternatives, modifications and variations which fall within the spirit and scope of the appended claims.

A portion of the disclosure of this patent document contains material to which is subject to a claim of copyright protection. The copyright owner has no objection to the facsimile reproduction by anyone of the patent document or the patent disclosure, as it appears in the Patent and Trademark Office patent file or records, but otherwise reserves all other rights whatsoever.

What is claimed is:

1. A grain damage measuring system comprising:
    a lamp for illuminating a grain sample with long wavelength ultraviolet electromagnetic radiation so that damaged portions of the grain may be distinguished from undamaged portions of the grain on the basis of electromagnetic radiation emitted by the sample and reflected from the sample;
    a video camera receiving the radiation reflected and emitted from the grain sample, forming an image therefrom and generating a video signal representing the image; and
    a signal processor comprising:
    means for digitizing the video signal into a plurality of discrete picture elements (pixels), each pixel having a value representing an intensity of a corresponding part of the image; and
    means for determining the number of pixels having values which exceed a predetermined threshold, said threshold being set so that pixel values exceeding the threshold correspond substantially only to portions of the image which represent damaged portions of the grain sample, said number being indicative of damage to the grain sample.

2. The grain damage measuring system of claim 1, wherein:
    the lamp illuminates the grain sample with radiation which causes only the damaged portions of the grain sample to flouresce.

3. The invention of claim 1, further comprising:
    a base;
    a motor supported by the base and having a shaft projecting therefrom, the motor rotating the shaft in response to signals applied thereto; and
    a bowl-shaped housing fixed to the shaft for rotation therewith, the bowl-shaped housing receiving the grain sample, rotation of the bowl causing mixing of the sample.

4. The invention of claim 3, wherein:
    the housing comprises a plurality of mixing paddles projecting from an inner surface of the housing, the paddles operating to mix the grain sample as the housing rotates.

5. The invention of claim 3, further comprising:
    means for automatically controlling rotation of the housing.

6. The invention of claim 3, wherein the signal processor comprises:
    means for successively obtaining and processing a plurality of images of a single grain sample; and
    means for generating a signal which causes a predetermined rotation of the housing prior to obtaining and processing of each image.

7. A system for measuring damage in a sample of grain, comprising:
    a housing for containing the grain sample;
    a motor for moving the housing in response to signals applied to the motor to cause mixing of the grain sample;
    a lamp for illuminating a grain sample with ultraviolet radiation to cause fluorescence of starch exposed in damaged portions of the grain sample so that the damaged portions of the grain may be distinguished from undamaged portions on the basis of electromagnetic radiation emitted by the sample and reflected from;
    a video camera receiving the radiation reflected and emitted from the grain sample, forming a plurality of images, and generating a video signal representing each image;
    an image analyzer and control unit comprising:
    means for digitizing the video signal into a plurality of discrete picture elements (pixels), each pixel having a value representing an intensity of a corresponding part of one of the images;
    means for determining for each image the number of pixels having values which exceed a predetermined threshold, said threshold being set so that pixel values exceeding the threshold correspond substantially only to portions of the image which represent damaged portions of the grain sample, said number being indicative of damage to the grain sample; and
    means for automatically generating motor control signals which cause the motor to move the housing and mix the grain sample so that each image represents a different arrangement of grain in the sample.

8. The invention of claim 7, further comprising:
    means for displaying each of said numbers.

9. The invention of claim 8, further comprising:

means for displaying each of said numbers and said cumulative average value.

10. The invention of claim 7, wherein the image analyzer and control unit further comprises:

means for deriving a cumulative average value from the number corresponding to the plurality of images.

* * * * *